United States Patent [19]

Resnick

[11] Patent Number: 4,567,003

[45] Date of Patent: Jan. 28, 1986

[54] 2,3-DIBROMO-PENTAFLUOROPROPYL FLUOROSULFATE

[75] Inventor: Paul R. Resnick, Wilmington, Del.

[73] Assignee: E. I. Du Pont de Nemours and Company, Wilmington, Del.

[21] Appl. No.: 592,919

[22] Filed: Mar. 22, 1984

[51] Int. Cl.$^4$ ............................................. C07C 141/02
[52] U.S. Cl. ................................. 260/458 F; 560/213
[58] Field of Search .................... 560/213; 260/456 F, 260/458 F

[56] References Cited

U.S. PATENT DOCUMENTS 4,206,138  6/1980  England ........................... 260/458 F
4,294,675 10/1981  Matsuda et al. ................. 204/159.14
4,401,829  8/1983  Schwertfeger ...................... 560/180

FOREIGN PATENT DOCUMENTS 0047947  3/1982  European Pat. Off. .

OTHER PUBLICATIONS

Clark, N. G. *Modern Organic Chemistry* (1964) Oxford Univ. Press. p. 90.
Paleta et al., Collection Czechoslov. Chem. Commun. 33, 2970–2982, (1968).
Yakubovitch, Zhurnal Obshchei Khimii, 31, 1995–2000 (1961).

*Primary Examiner*—Natalie Trousof
*Assistant Examiner*—L. Hendriksen

[57] ABSTRACT

Alkyl esters of $CF_2=CFCOOH$ can be prepared from $CF_2=CFCF_2OSO_2F$ by addition of bromine, reaction with $F^-$ to give $CF_2BrCFBrCOF$, esterification, and removal of bromine with zinc dust.

1 Claim, No Drawings

2,3-DIBROMO-PENTAFLUOROPROPYL FLUOROSULFATE

BACKGROUND OF THE INVENTION

Esters of perfluoroacrylic acid, $CF_2=CFCOOH$, are useful for making copolymers containing —COOR side chains, which may be converted to —COOH or —COO$^-$Na$^+$ groups for uses such as membranes for electrolysis, particularly the electrolysis of aqueous NaCl.

Prior processes for the synthesis of perfluoroacrylic acid esters include:

(1) a process wherein trichlorofluoromethane is added to 1,2-dichlorodifluoroethylene or carbon tetrachloride is added to chlorotrifluoroethylene to obtain 1,1,2-trifluoropentachloropropane, which is then oxidized and esterified to form a 2,3-dichlorotrifluoropropionic acid ester, followed by dechlorination of the ester; (2) a process wherein bromine is added to chlorotrifluoroethylene to obtain 1,2-dibromo-1-chlorotrifluoroethylene, which is then subjected to an addition reaction with propylene, followed by dehydrobromination to obtain 5-bromo-4-chloro-4,5,5-trifluoropentene-2 ($CF_2BrCFClCH=CHCH_3$), which is then oxidized and esterified to form a 3-bromo-2-chlorotrifluoropropionic acid ester, which is in turn dehalogenated; and (3) a process wherein chlorotrifluoroethylene is subjected to an addition reaction with hydrogen bromide, followed by dehalogenation to obtain trifluoroethylene, which is then subjected to an addition reaction with ICl, followed by dehydrochlorination to obtain trifluoroiodoethylene, which is then reacted with metallic magnesium in ether to form an organomagnesium intermediate, which is in turn reacted with carbon dioxide, followed by hydrolysis to obtain perfluoroacrylic acid, which is then esterified.

However, these processes have drawbacks in that they require cumbersome operations and expensive reactants and the total yield of the desired substance is extremely low.

An object of the present invention is to prepare $CF_2=CFCOOR$ by a high-yield process from readily available starting materials.

Another object is to prepare $CF_2=CFCOOR$ by a process which requires a minimum of purification of intermediate products.

SUMMARY OF THE INVENTION

The present invention provides a process for the conversion of $CF_2=CFCF_2OSO_2F$ to $CF_2=CFCOOR$, where R is a normal alkyl group with 1–4 carbon atoms, comprising (a) addition of bromine to the double bond of $CF_2=CFCF_2OSO_2F$, (b) purification of the product of step (a) to provide $CF_2BrCFBrCF_2OSO_2F$, (c) reacting the product of step (b) with F$^-$ to give $CF_2BrCFBrCOF$, (d) esterification of the product of step (c) with ROH, followed by purification, (e) debromination of the product of step (d) with Zn, and (f) recovery and purification of $CF_2=CFCOOR$.

These reactionss may be summarized:

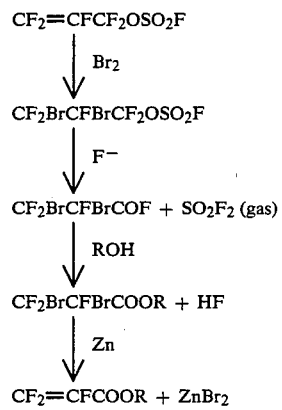

The starting material, perfluoroallyl fluorosulfate (FAF), $CF_2=CFCF_2OSO_2F$, may be prepared as described in U.S. Pat. No. 4,206,138 to D. C. England. England prepared FAF by reacting hexafluoropropylene with $SO_3$ under anhydrous conditions in the presence of a small amount of a trivalent boron compound such as trimethyl borate at 0°–100° C. A possible by-product is hexafluoropropylene sultone,

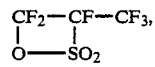

which is difficult to separate from FAF by distillation. The sultone in the FAF mixture can be hydrolyzed with ice water to give $CF_3CFHSO_2F+HF+CO_2$ (gas). This product, $CF_3CFHSO_2F$, is also difficult to separate from FAF by distillation, but it does not react with Br$_2$ and can be separated from the Br$_2$ adduct of FAF by distillation.

The addition of Br$_2$ to FAF, either pure or mixed with $CF_3CFHSO_2F$, can be carried out photochemically at −10° to +25° C., preferably 0°–10° C. The bromine is added slowly, and at the end of the reaction excess bromine is added to insure high conversion of FAF. Excess bromine is removed by washing with aqueous sodium bisulfate, and the desired product is separated. The product, $CF_2BrCFBrCF_2OSO_2F$, can be isolated by the distillation. It boils at 68°/50 mm Hg.

The next step, reaction of $CF_2BrCFBrCF_2OSO_2F$ with an alkali metal or quaternary ammonium fluoride, preferably KF, is carried out in a polar solvent free of reactive hydrogen atoms, such as glyme, $CH_3OCH_2CH_2OCH_3$, at 10°–150° C., preferably at 20°–105° C., with stirring. Sulfuryl fluoride, $SO_2F_2$, is evolved as a gaseous by-product and collected in a cold trap. If the condenser above the reaction vessel is not efficient, the trap contents can be evaporated to remove $SO_2F_2$, and the residue added to the reaction mixture.

Esterification may be carried out on the reaction mixture without isolating the acid fluoride. Reaction with a lower primary alcohol is exothermic, so the alcohol is added slowly. One may use methanol, ethanol, n-propanol, or n-butanol, but methanol is preferred. The temperature may be 20°–100°, preferably 25°–60° C.

The esterification mixture is mixed with cold water, and the organic layer, $BrCF_2CFBrCOOR$, is separated and purified.

The last step, debromination, is carried out with Zn and preferably a catalytic amount of iodine, in diglyme, (CH$_3$OCH$_2$CH$_2$)$_2$O. The product is isolated by distillation. A glyme solvent is chosen which can be separated from the alkyl perfluoroacrylate by distillation. In preparing CF$_2$=CF$_2$COOCH$_3$, for example, one does not use CH$_3$OCH$_2$CH$_2$OCH$_3$ because it boils too close to the desired product.

EXAMPLE 1

A 348.6 g mixture of

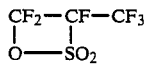

and CF$_2$=CFCF$_2$OSO$_2$F was slowly added with stirring to 168 g of ice water cooled in an ice bath. The reaction was vigorous and gas was evolved. After reaction was complete, the clear lower layer weighing 243.6 g and containing a mixture of CF$_2$=CFCF$_2$OSO$_2$F and CF$_3$CHFSO$_2$F was separated.

The 1060.9 g combined product of four such experiments was placed in a stirred flask, cooled in an ice bath, and irradiated with a GE sunlamp. Bromine was slowly added, and 150 ml of it reacted. Excess bromine was added and irradiation was continued for 40 minutes more. Excess bromine was destroyed by adding 100 ml water and 20% aqueous NaHSO$_3$ until no more bromine color was visible. The product was separated and distilled to give 909.9 g of CF$_2$BrCFBrCF$_2$OSO$_2$F, b.p. 68°/50 mm Hg. Its infrared and $^{19}$F nuclear magnetic resonance spectra were consistent with the assigned structure.

Auxiliary Example A

This example shows the reaction of hexafluoropropylene sultone with water, a reaction used in Example 1 to destroy the sultone. When 316 g of

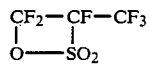

was slowly added with stirring to 168 g of ice water cooled in an ice bath, gas was evolved and 252.8 g (91.7%) of CF$_3$CHFSO$_2$F was obtained.

EXAMPLE 2

A flask was fitted with a magnetic stirrer, dropping funnel, thermometer, and water-cooled condenser topped by a dry-ice cooled condenser and N$_2$ bubbler. The flask was dried by flaming after adding 8.7 g KF. Glyme (80 ml) was added and stirred while 390 g of CF$_2$BrCFBrCF$_2$OSO$_2$F was slowly added. The reaction mixture was refluxed at 102° C. for 3 hours and stirred overnight at room temperature. Then 5 g more KF were added and the mixture was stirred at room temperature for 4 hours and at reflux for 90 minutes. The cold trap contained 103.7 g. After evaporation at room temperature the trap contained 7.5 g residue, which was added to the reaction mixture.

After cooling, 100 ml methanol was slowly added, resulting in an exothermic reaction. The mixture was stirred at room temperature for 10 minutes, then it was added to 2.3 liters of ice water. The lower layer was separated, washed with 1 liter of ice water, and dried with CaCl$_2$. Distillation gave 248.6 g (82.9%) CF$_2$BrCFBrCOOCH$_3$, b.p. 67°/20 mm.

EXAMPLE 3

To a stirred mixture of 49 g zinc dust, 0.3 g iodine and 240 ml (CH$_3$OCH$_2$CH$_2$)$_2$O was added a mixture of 150 g CF$_2$BrCFBrCOOCH$_3$ and 50 ml (CH$_3$OCH$_2$CH$_2$)$_2$O. An exothermic reaction took place and the reaction mixture was distilled to remove CF$_2$=CFCOOCH$_3$ and solvent. Redistillation gave 48.7 g (69.6%) CF$_2$=CFCOOCH$_3$, b.p. 84°–85° C.

I claim:
1. A compound having the formula CF$_2$BrCFBrCF$_2$OSO$_2$F.

* * * * *